United States Patent [19]
Kanegae et al.

[11] Patent Number: 5,508,191
[45] Date of Patent: Apr. 16, 1996

[54] MUTANT STRAINS OF AGROBACTERIUM FOR PRODUCING β-1,3-GLUCAN

[75] Inventors: Yukihiro Kanegae, Kobe; Akira Yutani, Himeji; Isamu Nakatsui, Kobe, all of Japan

[73] Assignee: Takeda Chemical Industries, Ltd., Osaka, Japan

[21] Appl. No.: 266,657

[22] Filed: Jun. 28, 1994

[30] Foreign Application Priority Data

Jul. 5, 1993 [JP] Japan .................. 5-165791

[51] Int. Cl.$^6$ .............. C12N 1/20; C08B 37/00; C08B 37/18
[52] U.S. Cl. .................. 435/252.2; 435/252.1; 435/101; 536/123.12; 536/124; 536/126
[58] Field of Search .................. 435/252.1, 101, 435/252.2; 536/123.12, 124, 126

[56] References Cited

U.S. PATENT DOCUMENTS

| | | | |
|---|---|---|---|
| 3,754,925 | 8/1973 | Kimura et al. | 99/1 |
| 4,355,106 | 10/1982 | Lawford | 435/101 |

OTHER PUBLICATIONS

Harada et al Agr. Biol. Chem. 29(8): 757–762 (1965).
Crueger et al, *Biotechnology: A Textbook of Industrial Microbiology*, 2nd ed, pp. 9–58 (1989).
Jacobson, in *Biotechnology, A Comprehensive Treatise in 8 Volumes*, Rehm et al, eds, pp. 297–299 (1981).
Harada et al., Agr. Biol. Chem., "Production of a Firm, Resilient Gel–Forming Polysaccharide by a Mutant of Alcaligenes faecalis var. myxogenes 10C3", vol. 30, No. 2, pp. 196–198 (1966).

*Primary Examiner*—John W. Rollins
*Assistant Examiner*—Francisco C. Prats
*Attorney, Agent, or Firm*—Wenderoth, Lind & Ponack

[57] ABSTRACT

Disclosed is a microorganism belonging to the genus Agrobacterium which is able to produce β-1,3-glucan and is either deficient or defective in phosphoenolpyruvate carboxykinase activity. Preferred microorganisms are mutants of Agrobacterium sp. biovar I. Particularly preferred mutant strains are Agrobacterium sp. biovar I GA-27 (FERM BP-4350) and Agrobacterium sp. biovar I GA-33 (FERM BP-4351).

5 Claims, No Drawings

MUTANT STRAINS OF AGROBACTERIUM FOR PRODUCING β-1,3-GLUCAN

FIELD OF THE INVENTION

The present invention relates to a method of, and microorganism for, producing β-1,3-glucan.

BACKGROUND OF THE INVENTION

β-1,3-glucans may be produced by microorganisms belonging to the genus Alcaligenes or Agrobacterium. One such glucan product, curdlan, is known [New Food Industry 20, 49 (1978), U.S. Pat. No. 3,754,925 etc].

Typical of such microorganisms is *Alcaligenes faecalis* var. myxogenes 10C3K (Agricultural Biological Chemistry 30, 196 (1966), etc.). Moreover, various mutants have been derived from this microorganism. These various mutants have been reported to include the uracil-requiring strain NTK-u (IFO 13140) and its non-uracil-requiring spontaneous mutants, namely ATCC 31749 and ATCC 31750 (U.S. Pat. No. 4,355,106).

In these references, phosphoenolpyruvate carboxykinase (the enzyme which catalyzes the reaction to convert oxaloacetic acid into phosphoenolpyruric acid) activity of the microorganisms is not disclosed.

*Alcaligenes faecalis* var. myxogenes 10C3 (IFO 13714) was subjected to taxonomic analysis and identified as Agrobacterium sp. biovar I in IFO Research Communications 15, 57–75 (1991) and List of Cultures 9th ed. (1992), both published by Institute for Fermentation, Osaka (IFO).

OBJECTS OF THE INVENTION

The main object of the present invention is to provide a method of, and microorganisms for, producing β-1,3-glucan.

This object as well as other objects and advantages of the present invention will become apparent to those skilled in the art from the following description.

SUMMARY OF THE INVENTION

The inventors of the present invention desired an industrially advantageous method of producing β-1,3glucan in high yields and with high efficiency. As a result of their research, the present inventors have found that a mutant strain obtained by subjecting *Alcaligenes faecalis* var. myxogenes 10C3K to treatment with a chemical mutagen was deficient in phosphoenolpyruvate carboxykinase activity and was unable to grow on media containing succinic acid as the sole carbon source, and that the method of using the mutant strain to produce β-1,3-glucan demonstrated high productivity and high yield.

Thus, the present invention relates to a method of producing β-1,3-glucan with high productivity and high yield.

According to the present invention, there is provided:

1) A microorganism belonging to the genus Agrobacterium which is able to produce β-1,3-glucan and is either deficient or defective in phosphoenolpyruvate carboxykinase activity, 2) The microorganism according to 1) above, wherein the microorganism is a mutant having phosphoenolpyruvate carboxykinase activity in the range of 0% to about 50% of its parent strain, 3) The microorganism according to 1) above, wherein the microorganism belongs to the genus Agrobacterium and is able to produce β-1,3-glucan but unable to grow on media containing succinic acid as the sole carbon source, 4) The microorganism according to 1) above, wherein the microorganism is Agrobacterium sp. biovar I, 5) The microorganism according to 4) above, wherein the microorganism is Agrobacterium sp. biovar I GA-27 (FERM BP-4350), 6) The microorganism according to 4) above, wherein the microorganism is Agrobacterium sp. biovar I GA-33 (FERM BP-4351), 7) A method of producing β-1,3-glucan which comprises cultivating the microorganism according to 1) above, in a culture medium so as to produce the β-1,3-glucan and then recovering the produced β-1,3-glucan, 8) The method according to 7) above, wherein the microorganism is a mutant having phosphoenolpyruvate carboxykinase activity in the range of 0% to about 50% of its parent strain, 9) The method according to 7) above, wherein the microorganism belongs to the genus Agrobacterium and is able to produce β-1,3-glucan but unable to grow on media containing succinic acid as the sole carbon source, 10) The method according to 7) above, wherein the microorganism is Agrobacterium sp. biovar I, 11) The method according to 10) above, wherein the microorganism is Agrobacterium sp. biovar I GA-27 (FERM BP-4350), 12) The method according to 10) above, wherein the microorganism is Agrobacterium sp. biovar I GA-33 (FERM BP-4351), 13) The method according to 7) above, wherein the β-1,3-glucan is curdlan, 14) The method according to 7) above, wherein the culture medium is a liquid medium, and 15) The method according to 7) above, wherein the microorganism is cultivated under aerobic conditions.

DETAILED DESCRIPTION OF THE INVENTION

The microorganisms belonging to the genus Agrobacterium, in the context of the present invention, include microorganisms which belong to the old generic name of Alcaligenes.

The β-1,3-glucan of the present invention is a polysaccharide comprising glucose units joined by, for the most part, β-1,3-glycosidic bonds, and has a degree of polymerization of about 100 to about 50,000, preferably, about 500 to about 40,000. Specific examples thereof are curdlan, paramylon and the like. In this invention, curdlan is preferred.

When the microorganism which is either deficient or defective in phosphoenolpyruvate carboxykinase (hereinafter referred to briefly as PEPCK) activity for use in the present invention is a mutant strain, the microorganism has PEPCK activity in the range of 0% to about 50%, preferably 0% to about 30%, of the corresponding activity of its parent strain. The assay of PEPCK activity can be performed by the method of R. J. Hansen et al. [Analytical Biochemistry 74,576, (1976), cf. the Reference Example described hereinafter]. When the microorganism of the present invention is not a mutant strain, the microorganisms having the same degree of PEPCK activity as the above mutant has can be used for the present invention. For example, such microorganism include those having PEPCK activity in the range of not more than about 0.006 ($\Delta E_{340}$/min/mg protein), preferably not more than about 0.004 ($\Delta E_{340}$/min/mg protein).

The microorganism of the present invention includes Agrobacterium sp. biovar I, among others. As preferred examples, there may be mentioned Agrobacterium sp. biovar I GA-27 (IFO 15490, FERM BP- 4350) and Agrobacterium sp. biovar I GA-33 (IFO 15491, FERM BP-4351), both of which can be produced by the procedure described hereinafter in Example 1.

The preferred microorganism of the present invention is a microorganism belonging to the genus Agrobacterium, which has an ability to produce a β-1,3glucan and cannot grow on a medium containing succinic acid as the sole carbon source. Nor can this strain grow, on media containing any other TCA cycle (tricarboxylic acid cycle, citric acid cycle)-associated organic acid than succinic acid, such as malic acid, fumaric acid, α-ketoglutaric acid, etc., or any TCA cycle-associated amino acid such as glutamic acid, aspartic acid, etc., as the sole carbon source.

Inability to grow in the context of this invention means that the particular microorganism shows little growth when it is cultivated on a solid medium containing 10 g/l of said TCA cycle-associated organic or amino acid as the sole carbon source (e.g. Medium B described hereinafter) at 32° C. for 48 hours. When a liquid medium is used as a test medium, the microorganisms is cultivated in the medium containing said organic or amino acid as the sole carbon source (e.g. Medium B described hereinafter) at 32° C. for 48 hours. The resulting culture broth is diluted 5-fold with deionized water and its optical density (OD) is determined with a spectrophotometer (e.g. Perkin-Elmer Spectrophotometer 35, cell dimensions 12×75 mm, the Perkin-Elmer Corporation) at the wavelength of 590 nm. When the OD value is not more than 0.03, the microorganism is assumed to have shown no growth.

The microorganism of the present invention can be obtained by subjecting its parent strain to a per se known method, such as UV irradiation, treatment with a chemical mutagen, e.g. N-methyl-N'-nitro-N-nitrosoguanidine (referred to as NTG) or nitrous acid etc.

For example, the parent strain is treated with a suitable amount, e.g. about 200 to about 500 µg/ml, of NTG at 32° C. for 30 minutes to induce its mutation and then treated cells are applied on a suitable medium e.g. an agar medium containing glucose as the sole carbon source. The resultant colonies is then replica-plated onto a medium containing succinic acid as the sole carbon sources and the colonies which grow on a medium containing glucose as the sole carbon source but do not grow or show only retarded growth on a medium containing succinic acid as the sole carbon sources (non-succinic acid-utilizing mutant) are picked. The microorganism of the present invention can also be obtained by using an organic acid, e.g. malic acid, fumaric acid, α-ketoglutaric acid, etc. or an amino acid, e.g. glutamic acid, aspartic acid, etc., which is associated with the TCA cycle (citric acid cycle), in lieu of succinic acid, to thereby derive a mutant not utilizing such acid.

The microorganism of the present invention, thus obtained, is grown on a culture medium. This culture medium may be a liquid medium or a solid medium. The use of a liquid medium is advantageous.

The principal sources of carbon that can be employed in the culture medium include glucose, fructose, sucrose, crude sugar, molasses (e.g., beet molasses, cane molasses, etc.) and saccharification products of various kinds of starch (e.g., tapioka starch, sago palm starch, sweet potato starch, potato starch, corn starch, etc.), among others. The concentration of such carbon sources used is about 3 to about 20% w/v, preferably about 5 to about 10% w/v, based on the medium. The addition of said carbon sources can be carried out in any suitable manner, i,e. addition of the required amount in a single dose at initiation of cultivation or sequential or continuous addition during cultivation to obtain the necessary amount.

There is no particular limitation on the composition of the medium, such as the amounts of the nitrogen sources, inorganic salts, etc., with the exception the carbon sources specified above. Thus, for example, the nitrogen sources include inorganic nitrogen sources such as ammonia, ammonium sulfate, ammonium chloride, urea, ammonium hydrogen phosphate, etc., ammonium salts of various organic substances (e.g. ammonium salts of organic acids such as succinic acid, fumaric acid, α-ketoglutaric acid, citric acid, malic acid, lactic acid, etc. and ammonium salts of acids such as glutamic acid, aspartic acid, etc.), and neutral amino acids such as alanine, proline, serine, threonine, histidine and so on. Examples of salts of phosphoric acid include potassium monohydrogen phosphate, potassium dihydrogen phosphate or ammonium hydrogen phosphate. These sources of nitrogen and salts of phosphoric acid can be used alone or in suitable combinations.

In addition, inorganic salts, such as the sulfates, hydrochlorides, carbonates or phosphates of inorganic substances, such as calcium, potassium, magnesium, manganese, iron, zinc, cobalt and copper, among other salts which are necessary for the microorganism to grow, can be used alone or in suitable combinations.

If necessary, peptone, meat extract, yeast extract, corn steep liquor, casamino acids, vitamins, etc. can be added alone or in suitable combinations. Furthermore, an antifoaming agent such as silicone oil and other additives may be added as necessary.

The cultivation is preferably carried out under aerobic conditions. The cultivation temperature is about 20° to about 40° C., preferably about 25° to about 35° C. The pH of the culture medium is about 4 to about 9, preferably about 5 to about 7, and can be adjusted using an acid or an alkali.

Regarding the cultivation time, the cultivation is continued until β-1,3-glucan production reaches maximum. Thus, the cultivation time is about 24 hours to about 10 days, preferably about 48 hours to about 5 days.

The β-1,3-glucan thus accumulated in the medium is recovered by a per se known procedure, (e.g. centrifugation, filtration, ultrafiltration etc.) and may be purified as necessary (e.g. U.S. Pat. No. 3,754,925 etc.)

The β-1,3-glucan obtained according to the present invention can be used in various fields, including the food, chemical and civil engineering industries.

As to food products, the β-1,3-glucan can be used as a thickener or viscosity builder, a binder or the like. Suitable food products include but are not limited to fish meat products (e.g. kamaboko, chikuwa, hampen, tempura, crab leg kamaboko, fish sausages, etc.), animal meat products (e.g. sausages, corned beef, roast ham, hamburgers, meat balls, etc.), cooked foods (e.g. gyoza, shao-mai, etc.), noodles (e.g. raw, steamed or boiled Chinese noodles, udon noodles, instant noodles, soba, roast soba, harusame, rice noodle, macaroni, spaghetti, gyoza wrapper, shao-mai wrapper, etc.), soybean products (e.g. tohu, frozen tohu, aburaage, gammodoki, etc.), seasonings (e.g. miso, sauces, ketchup, tare, etc.), beverages, pasty foods (e.g. jams, marmalade, peanut butter, flour paste, etc.), bean jams, gourmet food, dairy products (e.g. butter, margarin, cheese, whipped cream, etc.), rice balls and dumplings (e.g. warabi mochi, mitarashi dango, botamoti, etc.), rice and other cakes and confections (e.g. arare, okaki, sembei, candies, cookies, yokan, wanamagashi, fried cakes, Bavarian cream, mousse, cream puffs, marshmallows, chewing gum, ice cream, aspic jelly, etc.) and so on.

The β-1,3-glucan obtainable in accordance with this invention can be used, either as it is alone or in combination with other food materials, in the production of various types of food, including konjak-like foods, jelly fish-like foods, various jellies, shaped food articles such as sheet-form and somen-like foods, aspic jelly-like foods, shaped food articles made of cooked rice, edible film, low-calorie food, dietary fiber-containing food and so on.

In the chemical or civil engineering industries, for example, the β-1,3-glucan obtained by the present invention can be used as a segregation reducing agent for a hydraulic composition such as concrete or mortar.

The present invention makes it feasible to produce β-1,3-glucan at high productivity, in high yields based on carbohydrate and with high efficiency.

The following reference example and working examples are intended to illustrate this invention in further detail.

The mutants obtained in Example 1 given below, namely Agrobacterium sp. biovar I GA-27 and Agrobacterium sp. biovar I GA-33 have been deposited under the accession numbers of IFO 15490 and IFO 15491 at the Institute for Fermentation, Osaka (IFO 2-17-85, Juso Honmachi, Yodogawa-ku, Osaka-shi) since May 27, 1993, respectively, and under the accession numbers of FERM BP-4350 and FERM BP-4351 at the National Institute of Bioscience and Human-Technology, Agency of Industrial Science and Technology, Ministry of International Trade and Industry (1-1-3, Higashi, Tsukuba-shi, Ibaraki) since Jun. 24, 1994, respectively, according to the Budapest Treaty.

REFERENCE EXAMPLE

Assay of PEPCK Activity

Since the level of PEPCK activity is extremely low, Agrobacterium sp. biovar I 10C3k (referred to as the parent strain) was cultivated and the PEPCK activity of the parent strain was assayed as a preliminary study.

First, the parent strain was grown in a liquid medium, Medium B described hereinafter in Example 1, which contained glutamic acid as the sole carbon source (provided, however, that agar was not included). From the resultant culture broth, a crude enzyme was prepared as follows. The broth in the logarithmic growth phase of the parent strain was centrifuged to recover the cells. These cells were washed with 0.1M tris-hydrochloric acid buffer (pH7), suspended in the same buffer and disrupted by sonication. This cell suspension was centrifuged to remove the cell deblis. Thereafter ammonium sulfate was added gradually to 80% saturation, and then, the mixture was allowed to stand at 4° C. overnight. The mixture was further centrifuged and the precipitate was dissolved and dialyzed against the same buffer. The dialyzate was used as an enzyme sample.

According to the method of Hansen et al., the change ($\Delta E_{340}$/min) in absorbance of the above enzyme sample at 340 nm in each respective reaction systems shown below in Table 1 was determined using a spectrophotometer (Shimadzu Spectrophotometer UV-160). The results are shown in Table 1.

The above-mentioned method of Hansen et al. is based on the fact that PEPCK is an enzyme which catalyzes the reaction (as well as the reverse of the reaction) of phosphoenolpyruvic acid+ADP+$CO_2$→oxaloacetic acid+ATP (as a catalyst, $Mn^{2+}$ is necessary). In the presence of malate dehydrogenase, oxaloacetate is reduced by NADH to malate. The amount of NADH decreased in this reaction is stoichiometric with the amount of oxaloacetate. The rate of the decrease of NADH is determined by means of its change in absorbance at 340 nm.

TABLE 1

| Reaction system | $\Delta E_{340}$/min/ml |
|---|---|
| Complete system (phosphoenolpyruvic acid, ADP, $HCO_3^-$, $MnCl_2$) | 0.239 (100%) |
| Phosphoenolpyruvic acid eliminated | 0.014 (6%) |
| ADP eliminated | 0.012 (5%) |
| $HCO_3^-$ eliminated | 0.013 (5%) |
| $MnCl_2$ eliminated | 0.013 (5%) |
| IDP added in lieu of ADP | 0.018 (8%) |
| GDP added in lieu of ADP | 0.020 (8%) |
| $MgCl_2$ added in lieu of $MnCl_2$ | 0.020 (8%) |
| Pyruvic acid added in lieu of phosphoenolpyruvic acid | 0.016 (7%) |
| Malic dehydrogenase eliminated | 0.240 (100%) |

It is clear from the above results that this reaction requires phosphoenolpyruvic acid, ADP, $HCO_3^-$ and $MnCl_2$, that neither IDP nor GDP can be a substitute for ADP, that $MgCl_2$ cannot be a substitute for $MnCl_2$, either, and that pyruvic acid cannot be substituted for phosphoenolpyruvic acid. It was, thus, confirmed that this reaction is catalyzed by PEPCK.

In this assay of PEPCK activity, the enzyme sample used was not fully purified but contained malic dehydrogenase and, therefore, the addition of malic dehydrogenase was not necessary.

PEPCK activity ($\Delta E_{340}$/min/mg protein) is the activity found by subtracting the $\Delta E_{340}$/min/ml of the ADP-free (ADP eliminated) system from the $\Delta E_{340}$/min/ml of the complete system described in Table 1 and converting the difference to a value of activity per milligram protein. The amount of the protein in the enzyme is determined by the method of Lowry et al. (J. Biol. Chem., 193, 265 (1951)).

The amount of the protein in the enzyme of the parent strain was 1.18 mg/ml. The PEPCK activity ($\Delta E_{340}$/min/mg protein) of this parent strain was 0.192 [(0.239–0.012)/1.18= 0.192].

EXAMPLE 1

Agrobacterium sp. biovar I 10C3K (the parent strain) was treated with 200 μg/ml of NTG at 32° C. for 30 minutes for inducing mutation and applied to a medium (Medium A) of the composition shown under Medium A in Table 2. After confirmation of growth (32° C., 2 days), the colonies was replica-plated on a medium (Medium B) of the composition shown under Medium B in Table 2.

The microorganisms which showed no growth or only retarded growth (non-glutamic acid-utilizing mutants) were picked and named Agrobacterium sp. biovar I GA-27 and Agrobacterium sp. biovar I GA-33.

TABLE 2

| Component | Medium A (g/l) | Medium B*3 (g/l) |
| --- | --- | --- |
| Glucose | 10 | — |
| Glutamic acid | — | 10 |
| $(NH_4)_2HPO_4$ | 1.5 | 1.5 |
| $KH_2PO_4$ | 1.0 | 1.0 |
| $MgSO_4.7H_2O$ | 0.5 | 0.5 |
| $FeSO_4.7H_2O$ | 0.05 | 0.05 |
| $CaCl_2.2H_2O$ | 0.05 | 0.05 |
| $MnSO_4.4\text{-}6H_2O$ | 0.02 | 0.02 |
| $ZnCl_2$ | 0.001 | 0.001 |
| $CoCl_2$ | 0.001 | 0.001 |
| Agar*1 | 20 | 20 |
| pH*2 | 7.0 | 7.0 |

*1 Agar was eliminated in the case of liquid culture
*2 Adjusted with aqueous ammonia
*3 Glutamic acid was used as the sole carbon source The PEPCK activity of each of the mutants obtained was assayed by the same manner as in the Reference Example. Since the mutant scarcely grow on Medium B containing glutamic acid as the sole carbon source, the cells obtained by cultivation on Medium C described in Example 2 were used. The results are shown in Table 3.

TABLE 3

| Strain | PEPCK activity $\Delta E_{340}$/min/mg protein |
| --- | --- |
| GA-27 (FERM BP-4350) | 0.0035 (28%) |
| GA-33 (FERM BP-4351) | 0.0028 (22%) |
| Parent strain (10C3K) | 0.0127 (100%) |

It is clear from the above results that the PEPCK activity values of these mutants, Agrobacterium sp. biovar I GA-27 (FERM BP-4350, IFO 15490) and GA-33 (FERM BP-4351, IFO 15491), are as low as 28% and 22%, respectively, when the PEPCK activity of the parent strain is taken as 100%.

EXAMPLE 2

The seed medium as set forth in Table 4 was prepared and dispensed to 200 ml conical flasks at 20 ml per flask. Each of the flasks was autoclaved at 118° C. for 10 minutes. Each of the obtained media was inoculated with one loopful of the slant culture of Agrobacterium sp. biovar I GA-27 (FERM BP-4350), Agrobacterium sp. biovar I GA-33 (FERM BP-4351) obtained in Example 1 or Agrobacterium sp. biovar I 10C3K, and cultivated at 32° C. for 24 hours to yield a seed culture broth.

As the main medium, Medium C described in Table 4 was prepared and dispensed to 200 ml conical flasks. After each of the flasks was autoclaved at 118° C. for 10 minutes, glucose which was autoclaved separately, was added into the flasks having the main medium.

The above-described seed culture showing full growth, 2 ml, was transferred to the main medium and cultivated at 32° C. for 96 hours. After completion of cultivation, sodium hydroxide was added at a final concentration of 1N so as to dissolve the curdlan produced in the culture broth and then the cells were removed by centrifugation. The obtained supernatant was appropriately diluted and assayed for total sugar content by the phenol-sulfuric acid method. Furthermore, the residual amount of glucose in the culture broth was determined using a glucose assay kit (produced by Technikon). The residual glucose content was subtracted from the total sugar content, and the figure was multiplied by a factor of 0.9 to obtain the amount of curdlan produced. The amount of curdlan produced, the residual glucose content (referred to as "residual glucose" in Table 5), and the yield of curdlan based on glucose (referred to as "curdian yield based on glucose" in Table 5) for the mutants of the present invention and the parent strain are shown in Table 5.

TABLE 4

| Component | Seed medium | Main medium (Medium C) |
| --- | --- | --- |
| Glucose | 10.0 g/l | 75.0 g/l |
| Succinic acid | — | 2.5 g/l |
| Aqueous ammonia | — | 3.5 mg/l |
| $(NH_4)_2HPO_4$ | 1.5 g/l | — |
| $KH_2PO_4$ | 1.0 g/l | 1.0 g/l |
| $MgSO_4.7H_2O$ | 0.5 g/l | 0.5 g/l |
| $FeSO_4.7H_2O$ | 0.1 g/l | 0.005 g/l |
| $MnSO_4.4\text{-}6H_2O$ | 0.02 g/l | — |
| $ZnCl_2$ | 1.0 mg/l | 0.1 mg/l |
| $CoCl_2$ | 1.0 mg/l | 0.1 mg/l |
| $CaCO_3$ | 3.0 g/l | — |
| $CuSO_4.5H_2O$ | — | 0.1 mg/l |
| $CaCl_2.2H_2O$ | — | 0.01 g/l |
| pH (aqueous ammonia) | 7.2 | 7.5 |

TABLE 5

| Strain | Amount of Curdlan produced (mg/ml) | Residual glucose (mg/ml) | Curdlan yield based on glucose (%) |
| --- | --- | --- | --- |
| GA-27 (FERM BP-4350) | 38.6 | 1.2 | 52.3 |
| GA-33 (FERM BP-4351) | 40.9 | 0.3 | 54.7 |
| Parent (10C3K) | 34.0 | 7.5 | 50.3 |

*: Curdlan yield based on glucose = (amount of curdlan produced/glucose utilized) × 100

From Table 5, it is seen that the amount of curdlan produced by both mutants, GA-27 and GA-33, are greater than that produced by the parent strain. The curdlan yield based on glucose with GA-33 was higher than that with the parent strain by at least about 4% and this difference is of economic significance for the commercial production of β-1,3-glucans.

EXAMPLE 3

The seed medium described in Table 6 was prepared and dispensed to 200 ml conical flasks at 20 ml per flask. Each of the flasks was autoclaved at 118° C. for 10 minutes. Then, the medium was inoculated with one loopful of the slant culture of Agrobacterium sp. biovar I 10C3K, Agrobacterium sp. biovar I GA-27 (FERM BP-4350) or Agrobacterium sp. biovar I GA-33 (FERM BP- 4351) and cultivated at 32° C. for 24 hours to yield a seed culture broth.

The main medium, except for glucose, described in Table 6 was prepared and poured into a 5-liter jar fermenter and sterilized. Glucose was sterilized separately. After the glucose was added to the medium, 125 ml of the seed culture broth which showed full growth was transferred to the main medium and incubated under the conditions of 700 rpm agitation, 1.0 l/min. aeration, 2.5 l liquid volume and 32° C., until the added glucose had been completely consumed. To the resultant culture broth was added sodium hydroxide at a final concentration of 1N and the amount of curdlan produced was determined in the same manner as in Example 2. The results are shown in Table 7.

Furthermore, 100 ml of 1N-sodium hydroxide was added to 20 ml of the above culture broth and the resultant mixture was stirred for about 1 hour to dissolve the product curdlan. The cells were then removed by centrifugation (9000 rpm, 10 minutes). Upon neutralization with 4N HCl, a pasty neutralized gel was obtained. This gel-containing solution was centrifuged and the precipitated fraction was washed with deionized water and again centrifuged (9000 rpm, 10 minutes). The above procedure was repeated twice for sufficient desalting and the precipitate was washed with acetone, centrifuged and dried under reduced pressure to recover a curdlan in powder form. A 200 mg portion of this curdlan was subjected to swelling in 10 ml of deionized water, homogenized and degassed, after which it was put in a test tube and heated at 100° C. for 10 minutes. In this manner, a heat-gelable product (thermally coagulated gel) was obtained. The gel strength of this gel was measured with a rheometer (SUN Scientific Co., Ltd.). The results are shown in Table 7.

TABLE 6

| Component | Seed medium | Main medium |
|---|---|---|
| Glucose | 10.0 g/l | 75.0 g/l |
| Succinic acid | 1.5 g/l | 2.5 g/l |
| Aqueous ammonia | 2.0 ml/l | 3.5 ml/l |
| $KH_2PO_4$ | 1.0 g/l | 1.0 g/l |
| $MgSO_4 \cdot 7H_2O$ | 0.5 g/l | 0.5 g/l |
| $FeSO_4 \cdot 7H_2O$ | 0.1 g/l | 0.005 g/l |
| $MnSO_4 \cdot 4-6H_2O$ | 0.02 g/l | 0.002 g/l |
| $ZnCl_2$ | 0.001 g/l | 0.05 mg/l |
| $CoCl_2$ | 0.001 g/l | 0.05 mg/l |
| $CuSO_4 \cdot 5H_2O$ | — | 0.05 mg/l |
| Antifoam agent* | — | 1.0 ml/l |
| pH (aqueous ammonia) | 7.6 | 7.5 |

*Silicone oil (Shin-Etsu Chemical Co., Ltd.)

TABLE 7

| Strain | Cultivation time (hr.) | Amount of Curdlan produced (mg/ml) | Gel strength (g/cm$_2$) |
|---|---|---|---|
| GA-27 (FERM BP-4350) | 90 | 38.6 | 998 |
| GA-33 (FERM BP-4351) | 84 | 41.3 | 1020 |
| Parent (10C3K) | 93 | 37.2 | 986 |

The above results indicate that the curdian-producing abilities of the mutants of this invention, GA-27 and GA-33, are by far higher than that of the parent strain.

EXAMPLE 4

The seed culture described in Table 6 was prepared and dispensed to 200 ml conical flasks at 20 ml per flask. Each of the flasks was autoclaved at 118° C. for 10 minutes. Then, the medium was inoculated with one loopful of the slant culture of Agrobacterium sp. biovar I 10C3K, Agrobactorium sp. biovar I GA-27 (FERM BP-4350) or Agrobacterium sp. biovar I GA-33 (FERM BP- 4351) and cultivated at 32° C. for 24 hours to yield a seed culture broth.

The main medium, except for glucose, described in Table 6 was prepared and poured into a 5-liter jar fermenter and sterilized. Glucose was sterilized separately. After one-half amount of the glucose was added to the medium, 125 ml of the above-described seed culture showed full growth, was transferred to the main medium and cultivated under the conditions of 800 rpm agitation, 1.0 l/min. aeration, 2.5 l liquid volume and 32° C. After 24 hours of cultivation, the remaining one-half of the glucose was added and the cultivation was continued until the added glucose had been completely consumed. The amount of curdlan produced and gel strength was determined in the same manner as Examples 2 and 3. The results are shown in Table 8.

TABLE 8

| Strain | Cultivation time (hr.) | Amount of Curdlan produced (mg/ml) | Gel strength (g/cm$_2$) |
|---|---|---|---|
| GA-27 (FERM BP-4350) | 85 | 39.7 | 1010 |
| GA-33 (FERM BP-4351) | 76 | 43.1 | 997 |
| Parent (10C3K) | 90 | 38.9 | 990 |

The above results indicate that even when glucose is added in two installments, the curdian-producing capabilities of the mutants of this invention are still higher than the capability of the parent strain.

EXAMPLE 5

Agrobacterium sp. biovar I GA-27, Agrobacterium sp. biovar I GA-33, both obtained in Example 1, and their parent strain (10C3K) were respectively grown in liquid medium, Medium B described in Table 2, each containing 10 g/l of glucose, succinic acid, glutamic acid, fumaric acid, Δ-ketoglutaric acid or malic acid, as the sole carbon source (32° C., 48 hours).

To investigate the degree of growth of the strain on each medium, each culture broth was diluted 5-fold with deionized water and the absorbance (optical density) at 590 nm was determined with a spectrophotometer (Perkin-Elmer Spectrophotometer 35, cell 12×75 mm, The Perkin-Elmer Corporation). The results are shown in Table 9.

TABLE 9

| Carbon source | Parent strain (10C3K) | GA-27 (FERM BP-4350) | GA-33 (FERM BP-4351) |
|---|---|---|---|
| Glucose | 0.120 | 0.110 | 0.112 |
| Succinic acid | 0.090 | 0.008 | 0.005 |
| Glutamic acid | 0.150 | 0.010 | 0.007 |
| Fumaric acid | 0.092 | 0.006 | 0.005 |
| α-Ketoglutaric acid | 0.105 | 0.012 | 0.008 |
| Malic acid | 0.086 | 0.009 | 0.004 |

Similarly, each of the strains was cultivated on solid media, Media B described in Table 2, each containing 10 g/l of glucose, succinic acid, glutamic acid, fumaric acid, Δ-ketoglutaric acid and malic acid described in Table 10, as the sole carbon source (32° C., 48 hours). The degrees of growth of each of the strains on the respective media were visually assessed. The results are shown in Table 10.

TABLE 10

| Carbon source | Parent strain (10C3K) | GA-27 (FERM BP-4350) | GA-33 (FERM BP-4351) |
|---|---|---|---|
| Glucose | ++ | ++ | ++ |
| Succinic acid | ++ | − | − |
| Glutamic acid | ++ | ± | − |
| Fumaric acid | ++ | − | − |
| α-Ketoglutaric acid | ++ | ± | − |
| Malic acid | ++ | − | − |

++: Good growth
+: Growth
±: Occasionally sparse growth
−: No growth

The above results show clearly that whereas the parent strain grows on media containing these organic or amino acids, respectively, as the sole carbon source, the mutants of the present invention, GA-27 and GA-33, do not grow appreciably on any of the media.

What is claimed is:

1. A biologically pure culture of a mutant strain of Agrobacterium sp. biovar I, which produces β-1,3-glucan, which has a phosphoenolpyruvate carboxykinase activity of about 0.006 $\Delta E_{340}$/min/mg protein or less and which is unable to grow in media containing succinic acid as a sole carbon source.

2. The biologically pure culture according to claim 1, wherein the mutant strain of Agrobacterium is Agrobacterium sp. biovar I GA-27 (FERM BP-4350).

3. The biologically pure culture according to claim 1, wherein the mutant strain of Agrobacterium is Agrobacterium sp. biovar I GA-33 (FERM BP-4351).

4. A microorganism which is Agrobacterium sp. biovar I GA-27 (FERM BP-4350).

5. A microorganism which is Agrobacterium sp. biovar I GA-33 (FERM BP-4351).

* * * * *